(12) United States Patent
Cruise et al.

(10) Patent No.: US 9,408,916 B2
(45) Date of Patent: Aug. 9, 2016

(54) POLYMER FILMS

(71) Applicant: MicroVention, Inc., Tustin, CA (US)

(72) Inventors: Gregory M. Cruise, Rancho Santa Margaria, CA (US); Gloria Hincapie, Tustin, CA (US); Clayton Harris, Tustin, CA (US); Yue Wu, Tustin, CA (US)

(73) Assignee: MicroVention, Inc., Tustin, CA (US)

( * ) Notice: Subject to any disclaimer, the term of this patent is extended or adjusted under 35 U.S.C. 154(b) by 32 days.

(21) Appl. No.: 14/491,813

(22) Filed: Sep. 19, 2014

(65) Prior Publication Data

US 2015/0079328 A1 Mar. 19, 2015

Related U.S. Application Data

(60) Provisional application No. 61/880,029, filed on Sep. 19, 2013.

(51) Int. Cl.
| | |
|---|---|
| C08F 120/56 | (2006.01) |
| A61K 47/32 | (2006.01) |
| A61L 31/14 | (2006.01) |
| A61L 31/16 | (2006.01) |
| A61K 9/00 | (2006.01) |
| C08F 220/56 | (2006.01) |
| C08F 222/10 | (2006.01) |
| C08F 222/38 | (2006.01) |

(52) U.S. Cl.
CPC ............ *A61K 47/32* (2013.01); *A61K 9/0024* (2013.01); *A61L 31/148* (2013.01); *A61L 31/16* (2013.01); *C08F 120/56* (2013.01); *C08F 220/56* (2013.01); *C08F 222/1006* (2013.01); *C08F 222/385* (2013.01); *Y10T 428/21* (2015.01)

(58) Field of Classification Search
CPC ....................................................... C08F 120/56
See application file for complete search history.

(56) References Cited

U.S. PATENT DOCUMENTS

| | | |
|---|---|---|
| 4,070,348 A | 1/1978 | Kraemer et al. |
| 4,157,323 A | 6/1979 | Yen et al. |
| 4,925,677 A | 5/1990 | Feijen |
| 5,417,982 A | 5/1995 | Modi |
| 5,545,423 A | 8/1996 | Soon-Shiong et al. |
| 5,635,215 A | 6/1997 | Boschetti et al. |
| 5,648,100 A | 7/1997 | Boschetti et al. |
| 5,662,935 A | 9/1997 | Motta |

(Continued)

FOREIGN PATENT DOCUMENTS

| | | |
|---|---|---|
| CN | 103709323 A | 4/2014 |
| EP | 0240424 B1 | 5/1991 |

(Continued)

OTHER PUBLICATIONS

STN search Feb. 2, 2016.*

(Continued)

*Primary Examiner* — David Sample
*Assistant Examiner* — Christopher Polley
(74) *Attorney, Agent, or Firm* — K&L Gates LLP; Louis C. Cullman; Brian J. Novak

(57) ABSTRACT

Biodegradable, cross-linked polymer films and methods of making the same are described. The polymer films can be used for preventing adhesions following surgery and/or delivering therapeutic agents.

23 Claims, 2 Drawing Sheets

(56) References Cited

U.S. PATENT DOCUMENTS

| | | |
|---|---|---|
| 5,759,578 A | 6/1998 | Soon-Shiong et al. |
| 5,879,709 A | 3/1999 | Soon-Shiong et al. |
| 5,906,997 A | 5/1999 | Schwartz et al. |
| 5,922,357 A | 7/1999 | Coombes et al. |
| 6,218,440 B1 | 4/2001 | Kitagawa |
| 6,248,363 B1 | 6/2001 | Patel et al. |
| 6,306,922 B1 | 10/2001 | Hubbell et al. |
| 6,309,669 B1 | 10/2001 | Setterstrom et al. |
| 6,403,569 B1 | 6/2002 | Achterrath |
| 6,548,081 B2 | 4/2003 | Sadozai et al. |
| 6,555,138 B1 | 4/2003 | Karlsson et al. |
| 6,569,463 B2 | 5/2003 | Patel et al. |
| 6,689,374 B2 | 2/2004 | Chu et al. |
| 6,790,456 B2 | 9/2004 | Vogel et al. |
| 6,794,370 B2 | 9/2004 | Achterrath |
| 6,923,988 B2 | 8/2005 | Patel et al. |
| 6,946,146 B2 | 9/2005 | Mulye |
| 7,070,809 B2 | 7/2006 | Goupil et al. |
| 7,094,369 B2 | 8/2006 | Buiser et al. |
| 7,144,588 B2 | 12/2006 | Oray et al. |
| 7,153,572 B2 | 12/2006 | Cooper et al. |
| 7,442,385 B2 | 10/2008 | Lewis et al. |
| 7,449,236 B2 | 11/2008 | Lanphere et al. |
| 7,462,366 B2 | 12/2008 | Lanphere et al. |
| 7,588,780 B2 | 9/2009 | Buiser et al. |
| 7,591,993 B2 | 9/2009 | Boschetti |
| 7,670,592 B2 | 3/2010 | Boschetti |
| 7,736,671 B2 | 6/2010 | DiCarlo et al. |
| 7,776,240 B2 | 8/2010 | Chu et al. |
| 7,794,755 B2 | 9/2010 | Figuly et al. |
| 7,838,035 B2 | 11/2010 | Figuly |
| 7,838,699 B2 | 11/2010 | Schwarz et al. |
| 7,842,377 B2 | 11/2010 | Lanphere et al. |
| 7,858,119 B1 | 12/2010 | Odidi et al. |
| 7,887,846 B2 | 2/2011 | Figuly |
| 7,897,179 B2 | 3/2011 | Mulye |
| 7,951,402 B2 | 5/2011 | Lanphere et al. |
| 8,062,673 B2 | 11/2011 | Figuly et al. |
| 8,110,226 B2 | 2/2012 | Li |
| 8,182,807 B2 | 5/2012 | Labhasetwar et al. |
| 8,201,689 B2 | 6/2012 | Kaern |
| 8,226,926 B2 | 7/2012 | Reb |
| 8,252,302 B2 | 8/2012 | Macdonald |
| 8,323,698 B2 | 12/2012 | Gu et al. |
| 8,323,794 B2 | 12/2012 | Chu et al. |
| 8,329,224 B2 | 12/2012 | Hall et al. |
| 8,367,099 B2 | 2/2013 | Herweck et al. |
| 8,383,758 B2 | 2/2013 | Papisov |
| 8,426,481 B2 | 4/2013 | Liu et al. |
| 8,617,132 B2 | 12/2013 | Golzarian et al. |
| 8,673,266 B2 | 3/2014 | Boschetti |
| 8,691,791 B2 | 4/2014 | Lewis et al. |
| 8,697,137 B2 | 4/2014 | Vogel et al. |
| 8,709,384 B2 | 4/2014 | Reb |
| 8,739,978 B2 | 6/2014 | Yoon et al. |
| 8,741,351 B2 | 6/2014 | Vogel et al. |
| 2002/0028243 A1 | 3/2002 | Masters |
| 2002/0068089 A1 | 6/2002 | Vogel et al. |
| 2002/0197326 A1 | 12/2002 | Vogel et al. |
| 2003/0183962 A1 | 10/2003 | Buiser et al. |
| 2003/0206864 A1 | 11/2003 | Mangin |
| 2004/0161466 A1 | 8/2004 | Lewis et al. |
| 2005/0267556 A1 | 12/2005 | Shuros et al. |
| 2006/0025560 A1 | 2/2006 | Inoue et al. |
| 2006/0069168 A1 | 3/2006 | Tabata et al. |
| 2006/0222596 A1 | 10/2006 | Askari et al. |
| 2006/0251582 A1 | 11/2006 | Reb |
| 2007/0213683 A1 | 9/2007 | Cassingham et al. |
| 2007/0237741 A1 | 10/2007 | Figuly et al. |
| 2007/0237742 A1 | 10/2007 | Figuly et al. |
| 2007/0237830 A1 | 10/2007 | Figuly |
| 2007/0237956 A1 | 10/2007 | Figuly et al. |
| 2008/0033366 A1 | 2/2008 | Matson et al. |
| 2008/0039890 A1 | 2/2008 | Matson et al. |
| 2008/0102029 A1 | 5/2008 | Fritz et al. |
| 2008/0113029 A1 | 5/2008 | Fritz et al. |
| 2008/0220077 A1 | 9/2008 | Vogel et al. |
| 2009/0029077 A1 | 1/2009 | Atanasoska et al. |
| 2009/0092677 A1 | 4/2009 | Richard |
| 2009/0117033 A1 | 5/2009 | O'Gara |
| 2009/0164013 A1 | 6/2009 | Cruise et al. |
| 2009/0246275 A1 | 10/2009 | O'Gara et al. |
| 2010/0028260 A1 | 2/2010 | Fritz et al. |
| 2010/0040688 A1 | 2/2010 | Elbert et al. |
| 2010/0166876 A1 | 7/2010 | Lewis et al. |
| 2010/0261646 A1 | 10/2010 | Lavik et al. |
| 2011/0009327 A1 | 1/2011 | Hill et al. |
| 2011/0009520 A1 | 1/2011 | Figuly et al. |
| 2011/0033548 A1 | 2/2011 | Lai et al. |
| 2011/0033608 A1 | 2/2011 | Figuly et al. |
| 2011/0038936 A1 | 2/2011 | Griswold et al. |
| 2011/0082427 A1 | 4/2011 | Golzarian et al. |
| 2011/0091550 A1 | 4/2011 | Zhang et al. |
| 2011/0152765 A1 | 6/2011 | Weber et al. |
| 2011/0182998 A1 | 7/2011 | Reb et al. |
| 2011/0212179 A1 | 9/2011 | Liu |
| 2012/0129798 A1 | 5/2012 | Akala et al. |
| 2012/0213831 A1 | 8/2012 | Vogel et al. |
| 2012/0276151 A1 | 11/2012 | Lewis et al. |
| 2012/0289995 A1 | 11/2012 | Constant et al. |
| 2012/0302654 A1* | 11/2012 | Cruise .................. A61K 9/0024 521/149 |
| 2013/0052142 A1 | 2/2013 | Harder et al. |
| 2013/0190795 A1 | 7/2013 | Matson et al. |
| 2013/0315838 A1 | 11/2013 | Reb et al. |
| 2013/0323306 A1 | 12/2013 | Weber |
| 2014/0162969 A1 | 6/2014 | Lewis et al. |
| 2014/0186601 A1 | 7/2014 | Chang et al. |
| 2015/0079395 A1 | 3/2015 | Cruise et al. |
| 2015/0166696 A1 | 6/2015 | Plotkin et al. |
| 2015/0306227 A1 | 10/2015 | Cruise et al. |

FOREIGN PATENT DOCUMENTS

| | | |
|---|---|---|
| EP | 1534351 B1 | 10/2006 |
| EP | 1820495 A2 | 8/2007 |
| EP | 1267839 B1 | 10/2007 |
| EP | 2269580 A2 | 1/2011 |
| EP | 1796644 B1 | 4/2011 |
| EP | 1986706 B1 | 8/2011 |
| EP | 2368581 A2 | 9/2011 |
| EP | 2475695 B1 | 4/2014 |
| EP | 2286799 B1 | 7/2015 |
| JP | 2011-201031 A | 10/2011 |
| JP | 2011-245267 A | 12/2011 |
| JP | 2012-170773 A | 9/2012 |
| JP | 2012-187308 A | 10/2012 |
| JP | 2014-218439 A | 11/2014 |
| WO | 01/72281 A2 | 10/2001 |
| WO | 03/094930 A1 | 11/2003 |
| WO | 2006/081517 A2 | 8/2006 |
| WO | 2006/119968 A2 | 11/2006 |
| WO | 2007/035296 A2 | 3/2007 |
| WO | 2007/133020 A1 | 11/2007 |
| WO | 2008/034911 A1 | 3/2008 |
| WO | 2008/128580 A1 | 10/2008 |
| WO | 2008/136536 A1 | 11/2008 |
| WO | 2008/136563 A1 | 11/2008 |
| WO | 2009/015281 A2 | 1/2009 |
| WO | 2009/040434 A1 | 4/2009 |
| WO | 2010/063630 A2 | 6/2010 |
| WO | 2011/014722 A2 | 2/2011 |
| WO | 2011/068455 A1 | 6/2011 |
| WO | 2012/073188 A1 | 6/2012 |
| WO | 2012/121073 A1 | 9/2012 |
| WO | 2013/130143 A2 | 9/2013 |
| WO | 2013/177364 A1 | 11/2013 |
| WO | 2014/034787 A1 | 3/2014 |
| WO | 2015/042461 A1 | 3/2015 |

(56) References Cited

FOREIGN PATENT DOCUMENTS

| WO | 2015/042462 A1 | 3/2015 |
| WO | 2015/070094 A1 | 5/2015 |

OTHER PUBLICATIONS

Blinova et al., Poly(ethylene glycol) containing functionalized polymer membranes for carbon dioxide separation. Preprints-American Chemical Society, Division of Energy & Fuels, 59(1):433-434 (2014).

International Search Report and Written Opinion mailed on Dec. 24, 2014 for International Application No. PCT/US2014/056647 filed on Sep. 19, 2014.

International Search Report and Written Opinion mailed on Feb. 27, 2015 for International Application No. PCT/US2014/064680 filed on Nov. 7, 2014.

International Search Report and Written Opinion mailed on Dec. 24, 2014 for International Application No. PCT/US2014/056644 filed on Sep. 19, 2014.

Kamitani et al., Design of cell-surface-retained polymers for artificial ligand display. ChemBioChem, 10(2):230-233 (2009).

\* cited by examiner

POLYMER FILMS

CROSS REFERENCE TO RELATED APPLICATIONS

This application claims the benefit of U.S. provisional patent application No. 61/880,029, filed Sep. 19, 2013, the entire disclosure of which is incorporated herein by reference.

FIELD

Biodegradable polymer films for the prevention of tissue adhesions following surgery and/or for the delivery of therapeutic agents are described.

SUMMARY

Described herein generally are biodegradable, cross-linked films. The films can be biodegradable. The films can be utilized for the prevention of contamination following surgery and/or for the delivery of therapeutic agents.

These films can also be used during or after surgery, to cover a wound/abrasion, to seal a vessel, or the like. The films can be polymeric and include and/or be formed of one or more monomers and a crosslinker susceptible to chemical hydrolysis or enzymatic action. The polymer films can be used for preventing adhesions following surgery and/or delivering therapeutic agents.

Films can comprise a polymer including a reaction product of at least one monomer and at least one crosslinker; wherein the polymer is susceptible to degradation through chemical hydrolysis or enzymatic action. Films as described herein can have various thicknesses depending on a particular use, but generally can have a thickness between about 5 µm and about 1,200 µm.

Methods of making a polymer film as described herein are also described. These methods comprise: preparing an aqueous-based prepolymer solution including at least one monomer, at least one crosslinker susceptible to degradation through chemical hydrolysis or enzymatic action, and an initiator; and dispersing the aqueous-based prepolymer solution thereby forming the polymer film via polymerization.

Other methods can include the step of reacting a prepolymer solution to form a polymer film. The prepolymer solution can include at least one monomer comprising at least one functional group, at least one crosslinker susceptible to degradation, and an initiator.

Crosslinkers used to form the polymer films can impart biodegradability to the films. For example, the crosslinker can include at least one linkage susceptible to degradation through chemical hydrolysis or enzymatic action. The crosslinker can be glycidyl, glycidyl amino, or protein based. A glycidyl based crosslinker may be bis-glycidyl amino alcohol. A protein based crosslinker may be bi-functionalized methacryloyl-Ala-Pro-Gly-Leu-AEE-methacrylate.

DRAWINGS

DETAILED DESCRIPTION

Figure 1:
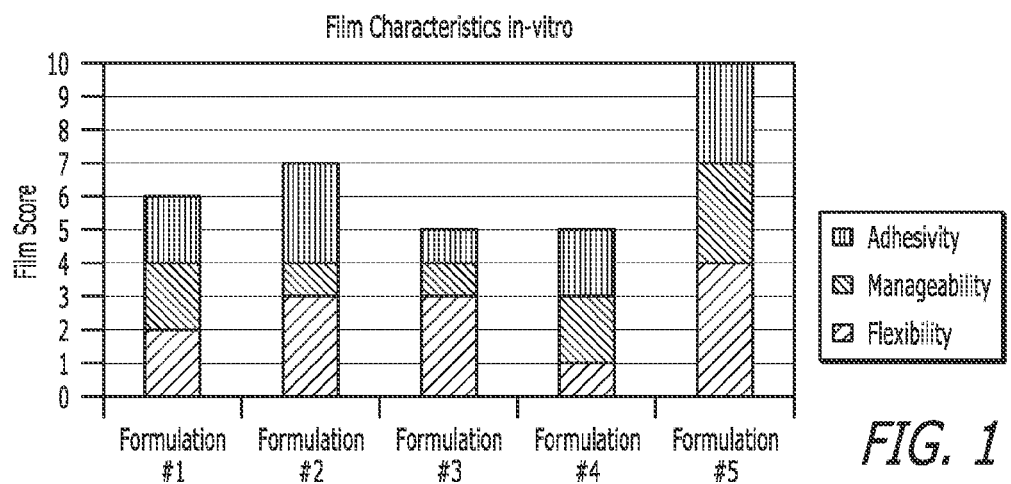
FIG. 1 is a graph showing various characteristics of different polymer films.

Described herein generally are polymeric films formed of or including a polymer material comprising a reaction product of one or more monomers and a crosslinker. The polymeric films described herein can be susceptible to cleavage by hydrolysis, oxidation, or reduction; by enzymatic or non-enzymatic means. The films can also be compressible and/or biodegradable, for ease of use.

The polymer or polymeric films can be formed from a prepolymer mixture or solution. The prepolymer solution can comprise: (i) one or more monomers that contain a singular functional group amenable to polymerization and (ii) one or more crosslinkers. In some embodiments, a polymerization initiator may be utilized.

In some embodiments, if one of the monomer(s) and/or crosslinker(s) is a solid, a solvent can be utilized in the preparation of the films, if liquid monomers and crosslinkers are utilized, a solvent may not be required. In some embodiments, even when using liquid monomers and crosslinkers, a solvent may still be used. Solvents may include any liquid that can dissolve or substantially dissolve a monomer, monomer mixture, and/or a crosslinker. Any aqueous or organic solvent may be used that dissolves the desired monomer(s), crosslinker(s), and/or polymerization initiators. In one embodiment, the solvent can be water. Additionally, solutes, e.g. sodium chloride, may be added to the solvent to increase the rate of polymerization.

Solvent concentrations in the prepolymer solutions can be about 10% w/w, about 20% w/w, about 30% w/w, about 40% w/w, about 50% w/w, about 60% w/w, about 70% w/w, about 80% w/w, about 90% w/w, between about 20% w/w and about 80% w/w, between about 50% w/w and about 80% w/w, or between about 30% w/w and about 60% w/w of the solution.

Any type of crosslinking chemistry can be utilized to prepare the described polymer films. In some embodiments, for example crosslinking chemistries such as, but not limited to nucleophile/N-hydroxysuccinimide esters, nucleophile/halide, vinyl sulfone/acrylate or maleimide/acrylate can be used. In one example embodiment, free radical polymerization can be used. As such, monomers with a singular ethylenically unsaturated group, such as acrylate, acrylamide, methacrylate, methacrylamide, and vinyl, may be used when employing free radical polymerization.

Any amount of monomer can be used that allows for a desired final film with desired properties. Monomer concentration in the solvent in the prepolymer solution can be about 1% w/w, about 2% w/w, about 3% w/w, about 4% w/w, about 5% w/w, about 10% w/w, about 15% w/w, about 20% w/w, about 30% w/w, about 40% w/w, about 50% w/w, about 60% w/w, about 70% w/w, about 80% w/w, about 90% w/w, about 100% w/w, between about 1% w/w and about 100% w/w, between about 40% w/w and about 60% w/w, between about 50% w/w and about 60% w/w, or between about 40% w/w and about 50% w/w.

Monomers can be selected based on imparting desired chemical and/or mechanical properties to the polymer film. If desired, uncharged, reactive moieties can be introduced into the film. For example, hydroxyl groups can be introduced into the films with the addition of 2-hydroxyethyl acrylate, 2-hydroxymethacrylate, derivatives thereof, or combinations thereof to a monomer. Alternatively, uncharged, relatively unreactive moieties can be introduced into the films. For example, acrylamide, methacrylamide, methyl methacrylate, derivatives thereof, or combinations thereof can be added.

In one embodiment, films can be prepared from monomers having a single functional group suitable for polymerization. Functional groups can include those suitable to free radical polymerization, such as acrylate, acrylamide, methacrylate, and methacrylamide. Other polymerization schemes can include, but are not limited to nucleophile/N-hydroxysuccinimide esters, nucleophile/halide, vinyl sulfone/acrylate or maleimide/acrylate. Selection of the monomers is governed by the desired mechanical properties of the resulting film and minimizing the biological effects of degradation products.

In some embodiments, the monomer can additionally contain an ionizable functional group that is basic (e.g. amines, derivatives thereof, or combinations thereof). The amine group may be protonated at pHs less than the pKa of the amine, and deprotonated at pHs greater than the pKa of the amine. In other embodiments, the monomer can additionally contain an ionizable functional group that is acidic (e.g. carboxylic acids, sulfonic acids, derivatives thereof, or combinations thereof). The acid group may be deprotonated at pHs greater than the pKa of the acid, and protonated at pHs less than the pKa of the acid.

If the binding of positively charged drugs is desired, monomers with negatively charged moieties, e.g. carboxylic acids, or other acidic moieties can be polymerized into the films. Acidic, ionizable, ethylenically unsaturated monomers can include, but are not limited to acrylic acid, methacrylic acid, 3-sulfopropyl acrylate, 3-sulfopropyl methacrylate, derivatives thereof, combinations thereof, and salts thereof. On the other hand, if the binding of negatively charged drugs is desired, monomers with positively charged moieties, e.g. amines, or other basic moieties can be included. Basic, ionizable, ethylenically unsaturated monomers can include, but are not limited to amino ethyl methacrylate, aminopropyl methacrylate, derivatives thereof, combinations thereof, and salts thereof.

An additional factor in monomer selection can be desire for degradation products of the films to elicit a negligible response from the host. In other embodiments, there can be desire for degradation products of the films to elicit substantially no response from the host A crosslinker can include one or more polymerizable groups, can join monomer chains together, and permit the formation of films. Biodegradation can be imparted to the films by utilizing a crosslinker with linkages susceptible to degradation in a physiological environment. Over time in vivo, linkages can break and the polymer chains may no longer be bound together. The judicious selection of monomers permits the formation of water-soluble degradation products that diffuse away from the area of treatment and are cleared by the host. Linkages susceptible to hydrolysis, such as esters, thioesters, carbamates, and carbonates, or peptides degraded by enzymes can be used in biodegradable films.

In one embodiment, one or more crosslinkers can contain at least two functional groups suitable for polymerization and at least one linkage susceptible to breakage to impart biodegradation to the films. Linkages susceptible to breakage in a physiological environment or in vivo can include, but are not limited to those susceptible to hydrolysis, including esters, thioesters, carbamates, and carbonates, and those susceptible to enzymatic action, including peptides that are cleaved by matrix metalloproteinases, collagenases, elastases, and cathepsins. In some embodiments, multiple crosslinkers can be utilized to control degradation rate in a manner not possible with only one crosslinker. In one embodiment, at least one crosslinker is susceptible to hydrolysis and at least one crosslinker is susceptible to enzymatic degradation.

In some embodiments, the at least one linkage is a peptide cleavable by matrix metalloproteinases, a peptide cleavable by matrix collagenases, a peptide cleavable by matrix elastases, a peptide cleavable by matrix cathepsins, or a combination thereof.

In some embodiments, the polymers used to form the films can include a second crosslinker, including a second linkage selected from an ester, a thioester, a carbonate, a carbamate, a peptide cleavable by matrix metalloproteinases, a peptide cleavable by matrix collagenases, a peptide cleavable by matrix elastases, and a peptide cleavable by matrix cathepsins.

In still other embodiments, the polymers used to form the films can include a third, fourth, fifth or more crosslinkers each including the same or a different linkage.

Crosslinkers can include peptide based crosslinkers, carbonate based crosslinkers, dis glycidyl amine crosslinkers, TMP gly ester crosslinkers, dithioester crosslinkers, or jeffamine glycidyl amine crosslinkers. Preferred concentrations of the crosslinkers in the final product can be about 0.05% w/w, about 0.1% w/w, about 0.5% w/w, about 1.0% w/w, about 2.0% w/w, about 3.0% w/w, about 4.0% w/w, between about 0.1% w/w and about 4.0% w/w, between about 0.5% w/w and about 2% w/w, or between about 1% w/w and about 1.5% w/w. A skilled artisan understands how to calculate final concentrations based on the amount in solvent used in the prepolymer solution.

In one embodiment, crosslinkers can be peptide based compounds. In one embodiment, a peptide based crosslinker can be

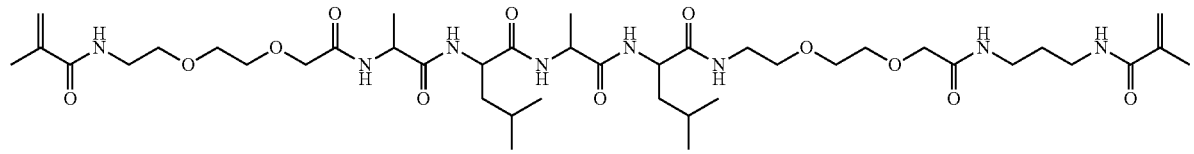 [SMILES: C=C(C)C(=O)NCCCNC(=O)COCCOCCNC(=O)C(CC(C)C)NC(=O)C(C)NC(=O)C(CC(C)C)NC(=O)C(C)NC(=O)COCCOCCNC(=O)C(=C)C]

or a derivative thereof. In another embodiment, the peptide based crosslinker can be or a derivative thereof.

In some embodiments, a peptide based crosslinker can be bi-functionalized methacryloyl-Ala-Pro-Gly-Leu-AEE-methacrylate.

In another embodiment, crosslinkers can have a structure wherein n is 1 to 20;
m is 1 to 20; and
X is O or S.

In another embodiment, the crosslinker can have a structure

In another embodiment, the crosslinker can have a structure

A crosslinker can also have a structure wherein o is 1 to 20; and
p is 1 to 20.

In one embodiment, the structure can be

A crosslinker can further have a structure

Wherein q is 1 to 10. In one embodiment, q is 1.

A crosslinker can also have a structure wherein r is 1 to 20; and
Y and Z are each independently selected from O, S, and NH.

In one embodiment, the crosslinker can have a structure or

-continued

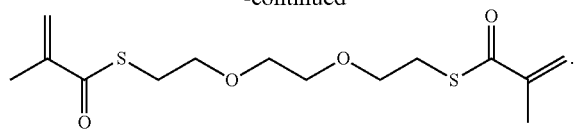

Further, in another embodiment, the crosslinker can have a structure

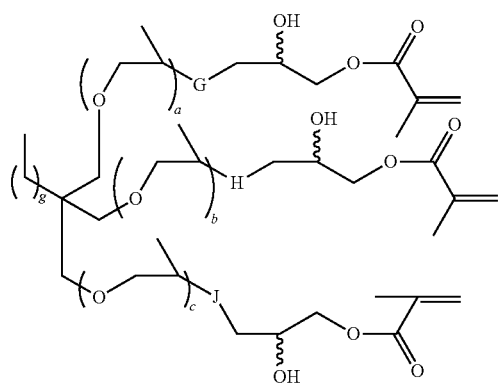

wherein G, H and J are each independently $CH_2$, O, S, NH, or not present,
a, b, and c are each independently 1 to 20; and
g is 1 to 20.

In another embodiment, a, b, and c are each independently 1 to 10. In still another embodiment, G, H and J are each independently O or NH.

In one embodiment, the crosslinker has a structure

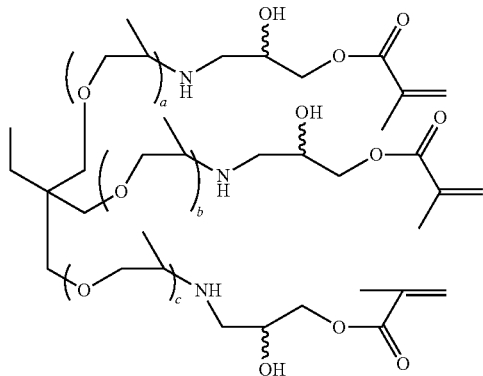

wherein a, b, and c are each independently 1 to 20.

Further, in another embodiment, the crosslinker can have a structure

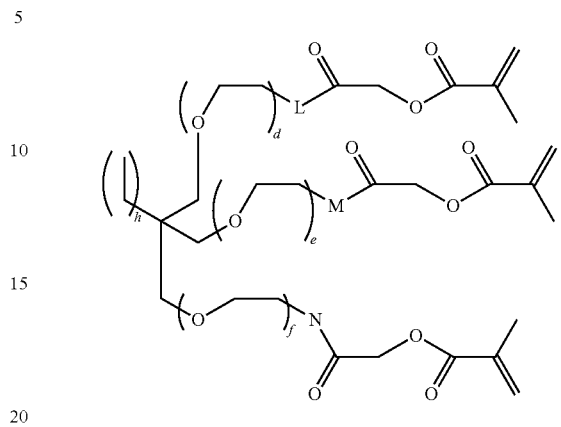

wherein L, M and N are each independently $CH_2$, O, S, NH, or not present,
d, e, and f are each independently 1 to 20; and
h is 1 to 20.

In another embodiment, d, e, and f are each independently 1 to 10. In still another embodiment, L, M and N are each independently O or NH.

In one embodiment, the crosslinker has a structure

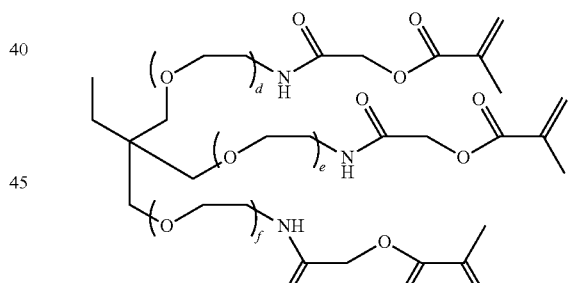

wherein d, e, and f are each independently 1 to 20.

A crosslinker can also have a structure

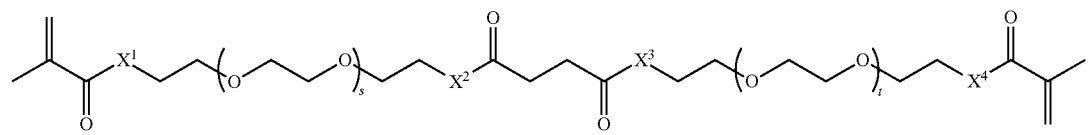

wherein s is 1 to 20;
wherein t is 1 to 20; and
$X^1$, $X^2$, $X^3$ and $X^4$ are each independently O or S.

In one embodiment, the structure can be

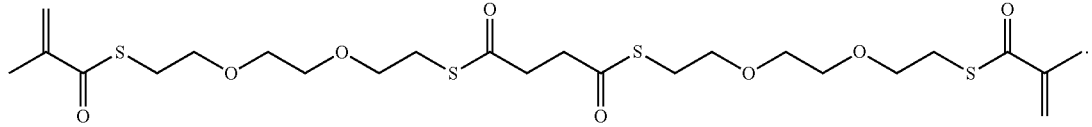 [SMILES: C=C(C)C(=O)SCCOCCOCCSC(=O)CCC(=O)SCCOCCOCCSC(=O)C(=C)C]

A crosslinker can also have a structure

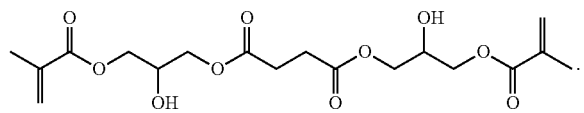 [SMILES: C=C(C)C(=O)OCC(O)COC(=O)CCC(=O)OCC(O)COC(=O)C(=C)C]

In some embodiments, a crosslinker can be a tetra ester, a tetra thioester or a dithio ester. In other embodiments, the crosslinker can be a peptide crosslinker or a carbonate crosslinker. A glycidyl based crosslinker may be bis-glycidyl amino alcohol.

Polymerization of the prepolymer solution can be by reduction-oxidation, radiation, heat, or any other method known in the art. Radiation cross-linking of the prepolymer solution can be achieved with ultraviolet light or visible light with suitable initiators or ionizing radiation (e.g. electron beam or gamma ray) without initiators. Cross-linking can be achieved by application of heat, either by conventionally heating the solution using a heat source such as a heating well, or by application of infrared light to the monomer solution. The free radical polymerization of the monomer(s) and crosslinker(s) is preferred and requires an initiator to start the reaction. In a preferred embodiment, the cross-linking method utilizes azobisisobutyronitrile (AIBN) or another water soluble AIBN derivative such as (2,2'azobis(2-methyl-propionamidine)dihydrochloride). Other cross-linking agents or initiators can include, but are not limited to N,N,N', N'-tetramethylethylenediamine, ammonium persulfate, benzoyl peroxides, and combinations thereof, including azobisisobutyronitriles. A preferred initiator can be a combination of N,N,N',N'-tetramethylethylenediamine and ammonium persulfate.

Polymer films can be produced or formed by methods including: reacting a prepolymer solution including at least one monomer including at least one functional group, at least one crosslinker susceptible to degradation, and an initiator; and forming the polymer film.

After the preparation of the films, they can be optionally dyed to permit visualization during preparation by the physician. Any of the dyes from the family of reactive dyes which bond covalently to the films can be used. Dyes can include, but are not limited to, reactive blue 21, reactive orange 78, reactive yellow 15, reactive blue No. 19, reactive blue No. 4, C.I. reactive red 11, C.I. reactive yellow 86, C.I. reactive blue 163, C.I. reactive red 180, C.I. reactive black 5, C.I. reactive orange 78, C.I. reactive yellow 15, C.I. reactive blue No. 19, C.I. reactive blue 21, or any of the color additives. Some color additives are approved for use by the FDA part 73, subpart D. In other embodiments, a dye that can irreversibly bond to the polymer matrix of the films may be used.

If the film does not bind any of the reactive dyes above adequately, a mononomer containing an amine can be added to the monomer solution in an amount to achieve the desired coloration. In some embodiments, even if the disclosed dyes do adequately bind to the films, a monomer containing an amine can still be added to the monomer solution. Examples of suitable monomers containing an amine include aminopropyl methacrylate, aminoethyl methacrylate, aminopropyl acrylate, aminoethyl acrylate, derivatives thereof, combinations thereof, and salts thereof. Preferred concentrations of the amine containing monomers in the final product can be less than or equal to about 1% w/w.

The polymer films can be prepared by polymerization between two plates separated by spaces. The plates can be formed of metal, glass or plastic. In one embodiment, the plates are formed of glass. The plates can be flat, curved or otherwise appropriately shaped. In some embodiments, the plates are flat. The monomer solution is placed or injected on a flat plate with pre-positioned spacers. The spacers can form any desired shape. A second flat plate is placed on top of the spacers, creating a thin space for the monomer solution.

After polymerization is complete, the top flat plate is removed and the polymer film is recovered from the bottom flat plate. The polymer film can then be washed to remove any and/or all residual monomers, solvent, or salt. Washing solutions include acetone, alcohols, water, and combinations thereof.

Polymerization can be allowed to proceed as long as necessary to produce films between the plates with desired resiliency. Polymerization can be allowed to proceed for about 1 hr, 2 hr, 3 hr, 4 hr, 5 hr, 6 hr, 7 hr, 8 hr, 9 hr, 10 hr, 11 hr, 12 hr, 18 hr, 24 hr, 48 hr, 72 hr, 96 hr, between about 1 hr and about 12 hr, between about 1 hr and about 6 hr, between about 4 hr and about 12 hr, between about 6 hr and about 24 hr, between about 1 hr and about 96 hr, between about 12 hr and about 72 hr, or at least about 6 hr.

Polymerization can be performed at a temperature to produce films with desired resiliency. Polymerization can be run at a temperature of about 10° C., about 20° C., about 30° C., about 40° C., about 50° C., about 60° C., about 70° C., about 80° C., about 90° C., about 100° C., between about 10° C. and about 100° C., between about 10° C. and about 30° C., at least about 20° C., at most about 100° C., or at about room temperature. In one embodiment, polymerization occurs at room temperature.

Further, the polymer films can be allowed to incubate for a given period of time to produce a desired resiliency. Incubation can be allowed to proceed for about 1 hr, 2 hr, 3 hr, 4 hr, 5 hr, 6 hr, 7 hr, 8 hr, 9 hr, 10 hr, 11 hr, 12 hr, 18 hr, 24 hr, 48 hr, 72 hr, 96 hr, between about 1 hr and about 12 hr, between about 1 hr and about 6 hr, between about 4 hr and about 12 hr, between about 6 hr and about 24 hr, between about 1 hr and about 96 hr, between about 12 hr and about 72 hr, or at least about 6 hr.

Incubation can proceed at any temperature that produces a film with a desired resiliency. Incubation can be performed at a temperature of about 10° C., about 20° C., about 30° C., about 35° C., about 37° C. about 40° C., about 50° C., about 60° C., about 70° C., about 80° C., about 90° C., about 100° C., between about 10° C. and about 100° C., between about 10° C. and about 30° C., at least about 20° C., at most about 100° C., or at about room temperature.

In one embodiment, polymerization is allowed to proceed for at least 2 hrs at room temperature followed by overnight incubation at 37° C.

After the polymerization is complete, the films may be washed to remove any solute, unreacted monomer(s), and/or unbound oligomers. Any solvent may be utilized, but care should be taken if aqueous solutions are used to wash films including polymers with linkages susceptible to hydrolysis. Preferred washing solutions can include, but are not limited to acetone, alcohols, water, saline, and combinations thereof.

Optionally, the washed films can then be dyed to permit visualization before injection into a microcatheter. A dye bath can be made by dissolving sodium carbonate and the desired dye in water. Films are added to the dye bath and stirred. After the dying process, any unbound dye is removed through washing. After dying and washing, the films can be packaged into vials or pouches, and sterilized.

Desired film thickness can be about 1 μm, about 2 μm, about 3 μm, about 4 μm, about 5 μm, about 6 μm about 7 μm, about 8 μm, about 9 μm, about 10 μm, about 15 μm, about 20 μm, about 30 μm, about 40 μm, about 50 μm, about 100 μm, about 200 μm, about 300 μm, about 400 μm, about 500 μm, about 600 μm, about 700 μm, about 800 μm, about 900 μm, about 1,000 μm, about 1,100 μm, about 1,200 μm, about 1,300 μm, about 1,400 μm, about 1,500 μm, about 1,600 μm, between about 5 μm and about 1,500 μm, between about 10 μm and about 500 μm, between about 100 μm and about 1,000 μm, at least about 1 μm, at least about 5 μm, at least about 50 μm, at least about 80 μm, at most about 1,500 μm, or at most about 1,200 μm.

Films can have any shape necessary to serve a required biological purpose. Shapes can be prefabricated including, but not limited to circles, squares, triangles, ellipses, pentagons, and the like. In some embodiments, one shape film can be formed and then custom cut to fit a desired location.

The films described herein can be sterilized without substantially degrading the polymer. After sterilization, at least about 50%, about 60%, about 70%, about 80%, about 90%, about 95%, about 99%, or about 100% of the film can remain intact. In one embodiment, the sterilization method can be autoclaving, gamma radiation, or ethylene oxide and can be utilized before administration.

In some embodiments, it may be desirable for the films to degrade over time, or in other words to be biodegradable. In such embodiments, the films can degrade to less than about 40%, about 30%, about 20%, about 10%, about 5% or about 1% intact after about 2 days, about 3 days, about 5 days, about 2 weeks, about 1 month, about 2 months, about 6 months, about 9 months, about a year, about 2 years, about 5 years, or about 10 years. In one embodiment, the films can be substantially degraded in less than about 1 month. In another embodiment, the films can be substantially degraded in less than about 6 months.

The films described herein can be compressible yet durable enough not to break apart or fragment. Substantially no change in the size or thickness of the films occurs during delivery. In other words, after delivery, the films described herein remain greater than about 60%, about 70%, about 80%, about 90%, about 95%, about 99%, or about 100% intact after delivery.

Further, the films can be cohesive enough to stick to the tissue and/or remain in place through friction with or between tissues. The films can further be prepared with an adhesive side in order to add tack to stick to tissues.

Example 1

Preparation of a Glycidyl-Based Crosslinker

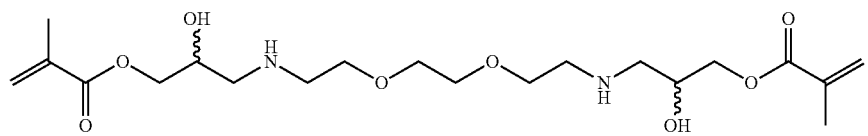 [SMILES: C=C(C)C(=O)OCC(O)CNCCOCCOCCNCC(O)COC(=O)C(=C)C]

To 10 g (67.6 mmol) of 2,2'-ethylenedioxy bis-ethylamine is mixed 10 g (70.4 mmol) of glycidyl methacrylate, and 3 g of silica gel (Aldrich 645524, 60 Angstrom, 200-425 mesh). After stirring for 1 hr, another 9 g (63.4 mmol) of glycidyl methacrylate was added and the suspension was stirred for additional 1.5 hr. The mixture was diluted with 200 mL chloroform and filtered through a 600 mL fritted glass Buchner to remove the silica gel. LC-MS analysis of the resultant chloroform solution shows a negligible amount of mono-glycidyl amino alcohol and mostly bis-glycidyl amino alcohol at $[M+H]^+$ m/z 433.2. The solution was concentrated to about 50 g in vacuo. The resultant heavy syrup was diluted to 100 mL with acetonitrile and stored at −80° C.

Example 2

Preparation of a Peptide-Based Crosslinker

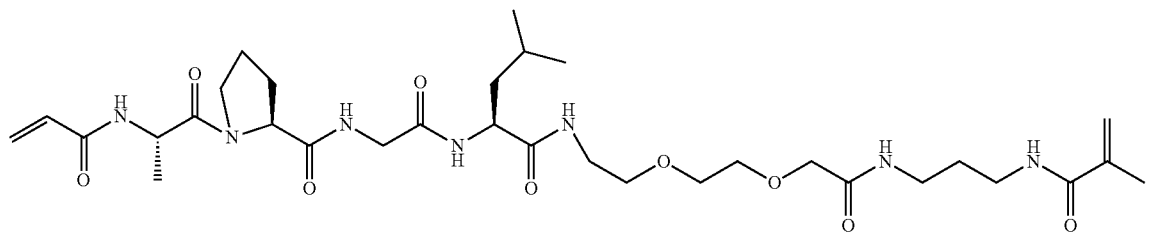 [SMILES: C=CC(=O)N[C@@H](C)C(=O)N1CCC[C@H]1C(=O)NCC(=O)N[C@@H](CC(C)C)C(=O)NCCOCCOCC(=O)NCCCNC(=O)C(=C)C]

A heterobifunctional, tetrapeptide (methacryloyl-Ala-Pro-Gly-Leu-AEE-methacrylate) was provided (Bachem, Torrance, Calif.). The peptide (653 mg, 1 mmole) was dissolved in 5 mL DMF and N-(3-aminopropyl)methacrylamide hydrochloride (190 mg, 1.1 mmol) and N,N-diisopropylethylamine (174 µL, 1 mmol) were added. After 2 hr, 20 mg butylated hydroxyltoluene was added. The reaction mixture was precipitated with 200 mL of ethyl ether. The solids were collected using centrifugation. The pellet was redissolved in a 90/5/5 solution of chloroform/methanol/methanol+10% aqueous ammonia and applied to 50 g of silica gel in a 5×20 cm column (Aldrich, 60 Angstrom, 200-425 mesh). The silica gel column was developed with 500 mL of 90/515 solution of chloroform/methanol/methanol+5% aqueous ammonia and the peptide containing eluent concentrated in vacuo to yield 110 mg of pale yellow oil. The pale yellow oil was dissolved in 10 mL of methanol and stored at −80° C. LC-MS analysis of the product showed the desired $[M+H]^+$ at m/z 680 and $[M+Na]^+$ at m/z 702.

Example 3

MA-AEEAc-ALAL-AEEAc-MA, ALAL Tetrapeptide Crosslinker

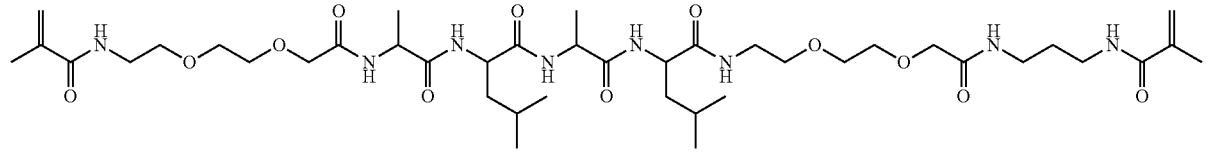 [SMILES: C=C(C)C(=O)NCCCNC(=O)COCCOCCNC(=O)C(CC(C)C)NC(=O)C(C)NC(=O)C(CC(C)C)NC(=O)C(C)NC(=O)COCCOCCNC(=O)C(=C)C]

To 841 mg (1 mmol) of NHS ester, MA-AEEAc-ALAL-AEEAc-NHS was added 179 mg of 3-aminopropyl methacrylate-HCl into a clean dry 15 mL flask with a dry stir bar and a dry septum, followed by 5 mL of dry dimethyl formamide. Upon stirring a clear solution resulted and 200 microliters (1 mmol) of diisopropylethylamine was added all at once. After one hour, the reaction mixture was transferred to a 250 mL pear shaped flask using 3×5 mL of MeOH and placed on the vacuum line overnight. The next day the reaction mixture was transferred to a scintillation vial with two mL of methanol, to give approx. 35% solids, and stored at −80° C. The crude crosslinker above gives a single HPLC peak gives $[M+H]^+$ at m/z of 869.9, molecular mass calculated for $C_{41}H_{72}N_8O_{12}$ is 868.5.

Example 4

Carbonate Crosslinkers

To 33 g (100 mmol) cesium carbonate suspended in 500 mL of 1:1 acetonitrile:methanol was added 17.2 g (200 mmol) of methacrylic acid over one hour with good stirring. After stirring for an additional two hours, solvent was removed from the reaction mixture and the residue was suspended in 500 mL of dry ether and collected by filtration onto a dry 600 mL Buchner funnel with a medium frit. After carefully rinsing the solids on the funnel with 200 mL dry ether several times, the solids were dried in the vacuum oven overnight to give 45 g of a hygroscopic beige powder (Compound A) which has to be quickly placed into a dry environment.

HEMA-1-Chloroethyl carbonate: To 24 mL of HEMA (200 mmol) in 1,000 mL of dry ether was added 16.8 mL (213 mmol) of pyridine at 4-10° C., under argon. To this solution was added 21.3 mL (200 mmol) of 1-chloroethyl chlorocarbonate, drop wise with stirring over hour. After stirring 2 hour at 4-10° C., the heavy precipitate (Compound B) is removed by filtration and the filtrate is concentrated to an oil in vacuo, yielding 44 g (100%).

To 4.4 g (20 mmol) of Compound B in 40 mL of anhydrous dimethyl formamide, was added 0.9 g (4.0 mmol) of Compound A at 100° C., under argon, with good stirring. After 15 min, another 1.2 g (5.4 mmol) of Compound A was added at 100° C., under argon, with good stirring followed by a final 0.9 g (4.0 mmol), under the same conditions, for a total of 2.9 g Compound A (13.4 mmol). The yellow brown reaction mixture was heated at 100° C. for an additional 3 hrs and after cooling to room temperature the solvent was removed in vacuo, and the residue was left on the vacuum line overnight. The residue was taken up in 50 mL of 1:1 Chloroform:Hexane and applied to a 750 gram gold column and eluted with Hexane then 0-20% Ethyl Acetate in Hexane. The following carbonate

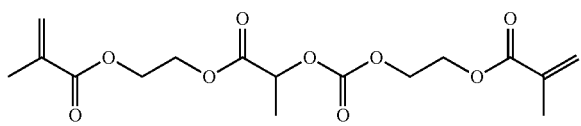 [SMILES: C=C(C)C(=O)OCCOC(=O)OC(C)C(=O)OCCOC(=O)C(=C)C]

came out starting at 27 min and the following carbonate

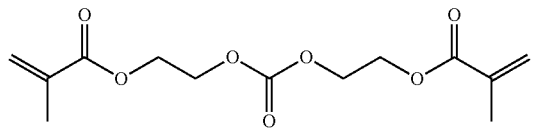 [SMILES: C=C(C)C(=O)OCCOC(=O)OCCOC(=O)C(=C)C]

came off at 32 min.

Example 5

TMP Gly Ester

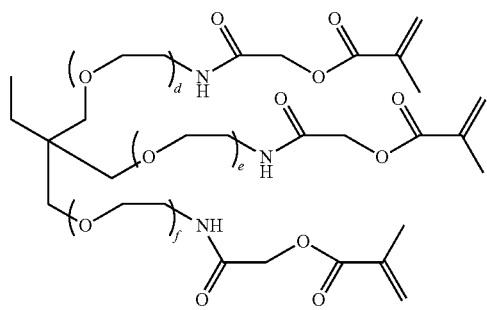

TMP-Chloroacetamide: To 13.2 grams of triamino trimethylol propane ethoxylate in 250 mL of dry tetrahydrofuran (THF) was added 6.32 g (80 mmol) of pyridine and this solution was added to 6.44 g of chloroacetyl chloride in 250 mL of THF with good stirring, at 4-10° C. under Ar. After stirring for fifteen minutes, the reaction mixture was warmed to room temperature and the THF and other volatile material were removed in vacuo. The resulting solids were dissolved into 200 mL of chloroform which was in turn washed with 100 mL of saturated aqueous sodium bicarbonate, dried over magnesium sulfate and the solvent was removed in vacuo.

TMP-NH-Gly-Methacrylate: To approx 15 g of material above dissolved into 75 mL of anhydrous dimethyl formamide was added 18 g of cesium methacrylate and the resulting suspension heated at 40-50° C. for 2 hrs.

After precipitation with 500 mL of chloroform, the inorganic salts were collected by filtration and the filtrate was concentrated to an oil in vacuo to give 18 g of a reddish brown oil. This oil could be polymerized with AIBN at 80° C., in IPA to a hard pellet. Chromatography on 6 g of this through a plug of the above silica with 1,200 mL of 2-20% methanol in chloroform, gave 6 g of light red colored material.

Example 6

Discrete Thio Ester

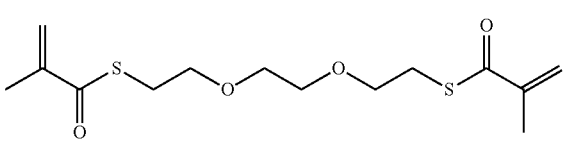 [SMILES: C=C(C)C(=O)SCCOCCOCCSC(=O)C(=C)C]

To 6.6 mL (40 mmol) 2,2'-(ethylenedioxy)dimethanethiol in 200 mL of tetrahydrofuran (THF) was added 20.9 mL of diisopropylethyl amine and the resulting dry solution was added to 11.5 mL of methacryloyl chloride (120 mmol) in 200 mL of dry THF, at −5° C., with good stirring over 1 hr. The reaction mixture was stirred at 0° C. for 1 hr and at 20° C. for one hour at which point 10 mL of isopropyl alcohol was added and the solvent was removed in vacuo.

The residue was applied to a 330 g silica (gold) column in a minimum volume of chloroform and the column was eluted with 0-5% isopropyl alcohol in methylene chloride at 200 mL/min. The fraction which eluted at 13-14 min as a single peak was isolated as 1.3 g of yellow oil. AIBN initiated reaction of 50 mg of this material displayed a hard pellet.

Example 7

Polymeric Thio Ester

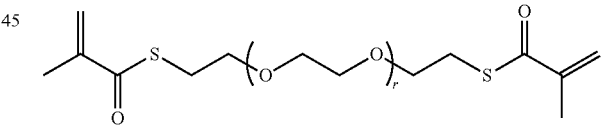

To 40 mL of dry tetrahydrofuran (THF), at 0° C., containing 0.4 mL (4 mmol) of methacryloyl chloride was added 20 mL of dry THF containing 2.0 g (1.33 mmol) of poly(ethylene glycol) dithiol 1,500 mw and 0.7 mL (4.0 mmol) diisopropylethylamine, dropwise over 5 min, with rapid stirring. After stirring for 2 hrs, the reaction mixture was warmed to room temperature and solvent was removed in vacuo. Then 100 mL of chloroform was used to dissolve the reaction mixture and this was removed in vacuo to entrain methacryloyl chloride.

The reaction mixture was placed on the vacuum line overnight at approximately 30 microns and a yellow solid formed.

AIBN initiated reaction of 50 mg of this in 50 microliters of isopropyl alcohol resulted in a sponge of yellow gel.

Example 8

Jeffamine Glycidyl Amine

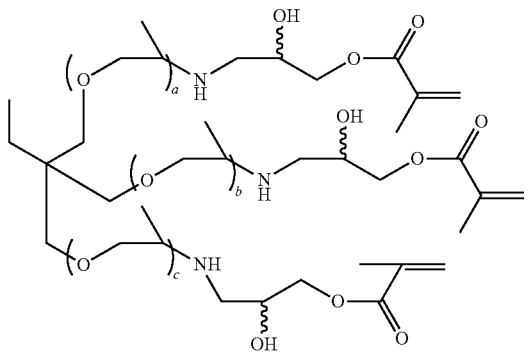

To 11 g Jeffamine (25 mmol) is added 10.5 g of glycidyl methacrylate (75 mmol) followed by 4 g silica gel and 100 mg butylated hydroxytoluene. The reaction mixture was stirred at 20° C. After 2 hrs, 50 mL of chloroform was added to the thickening reaction mixture and stirring was continued. After another eighteen hours, 200 additional mL of chloroform was added and the reaction mixture was filtered to remove silica gel and most of the solvent removed in vacuo. The residue was dissolved in 20 mL of isopropyl alcohol to give 40 mL of approximately 50% desired compound.

Example 9

Film Prepared with a Glycidyl-Based Crosslinker

The prepolymer solution was prepared by dissolving 1.4 g of 2-hydroxypropyl acrylate (HPA), 0.4 g of sodium acrylate, and 0.015 g of a glycidyl-based crosslinker from Example 1, in 4.0 g of distilled water. This solution was vacuum degassed for 5 min and flushed with argon.

An initiator solution was made by dissolving 0.25 g of ammonium persulfate in 1.0 g of distilled water. Additionally, two glass plates were prepared with 4 small dividers, such as a glass insert, placed at the four corners. This was wiped clean with isopropanol.

N,N,N',N'-Tetramethylethylenediamine (approximately 50 μL) was added to the prepolymer solution and the solution was mixed. After a minute, about 25 μL of the initiator solution was added to the prepolymer solution while stirring. This was then poured onto one of the previously prepared glass plates, covered with the second glass plate and a weight placed on top. This was allowed to polymerize over 2 hrs before being placed in a 37° C. oven overnight.

Example 10

Film Prepared with a Peptide Crosslinker

The prepolymer solution was prepared by dissolving 1.9 g acrylamide, 1.1 g sodium acrylate, and 0.1 g of a peptide-based crosslinker from Example 2 in 10.0 g of distilled water. This solution was vacuum degassed for 5 min and flushed with argon.

An initiator solution was made by dissolving 0.25 g of ammonium persulfate in 1.0 g of distilled water. Additionally, two glass plates were prepared with 4 small dividers, such as a glass insert, placed at the four corners. This was wiped clean with isopropanol.

N,N,N',N'-Tetramethylethylenediamine (approximately 64 μL) was added to the prepolymer solution and the solution mixed. After a minute, approximately 25 μL of the initiator solution was added to the prepolymer solution while stirring. This was then poured onto one of the previously prepared glass plates, covered with the second glass plate and a weight placed on top. This was allowed to polymerize over 2 hrs before being placed in a 37° C. oven overnight.

Example 11

Purification of Films

After the polymerization was complete, the plates were opened and the film cut to the desired size. These were then placed in a plastic beaker with solution for washing. The preferred method of washing is placing the films through an acetone solution gradient. For approximately 2 hrs, the films were suspended in 75% solvent, 80% solvent, 85% solvent, 90% solvent, 95% solvent, and 100% solvent. At this time, the films were allowed to stay in acetone overnight; the next day, the liquid was exchanged out for fresh solution. After approximately 6 hrs, the films were left without solvent to air-dry and/or placed in the vacuum oven overnight. Subsequently, the films were packaged, and sterilized.

Example 12

Determination of Film Adhesiveness on a Liver

To simulate the use of adhesion barrier films, prepared as in Example 9, a sample was placed on either porcine or bovine liver. The film was applied dry or pre-hydrated and irrigated once on the organ. The samples were tested for manageability, flexibility, sturdiness and adhesiveness over time. The grading scale for the samples were divided in three parts and added to come to a total maximum score of 10 points. Flexibility was scored as follows: (4) does not break easily after re-hydration, (2) breaks easily re-hydrated, and (1) stiff, crumbles under pressure. Manageability was scored as follows: (3) easily manageable, not sticky, to (1) gummy and sticks to itself. Adhesiveness was scored as follows: (3) strong adhesivity, (2) some adhesivity, but dislodged easily, and (1) no adhesivity. FIG. 1 illustrates data for a variety of monomers used for polymer film preparation in Example 9.

Example 13

Determination of In Vitro Degradability

Figure 2:
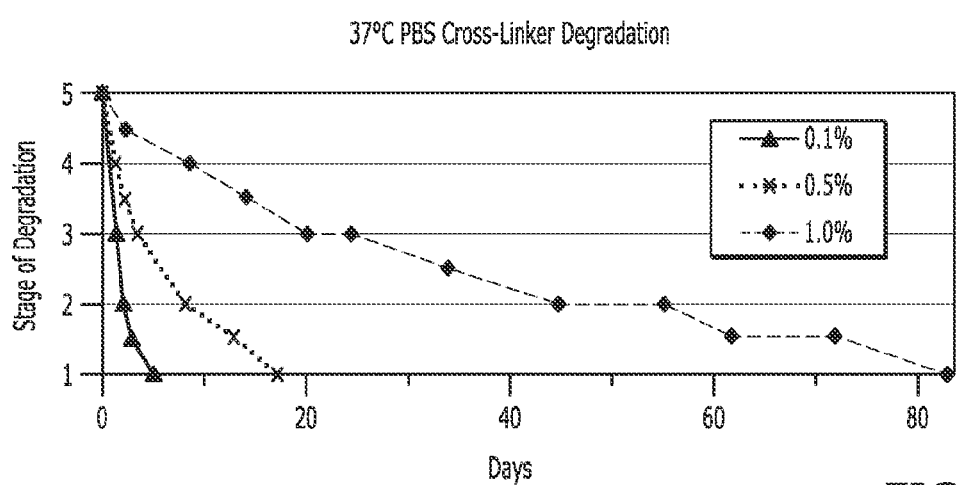
FIG. 2 is a graph showing the progression of degradation for different polymer films.

A 1"×1" sample of the polymer film prepared as in Example 9 was placed in a 50 mL conical tube with 45 mL of 0.01 M phosphate buffered saline. The samples were placed in a 37° C. and a 55° C. oven for monitoring. The visual analysis included transparency of the film, integrity of the edges, sturdiness of the film, and the viscosity of the film in solution. The grading scale for the samples included (5) sturdy film with clear edges, (3) large gelatinous mass that still maintains film structure, and (1) viscous liquid with no apparent solid mass. Grading results are illustrated in FIG. 2.

Figure 3:
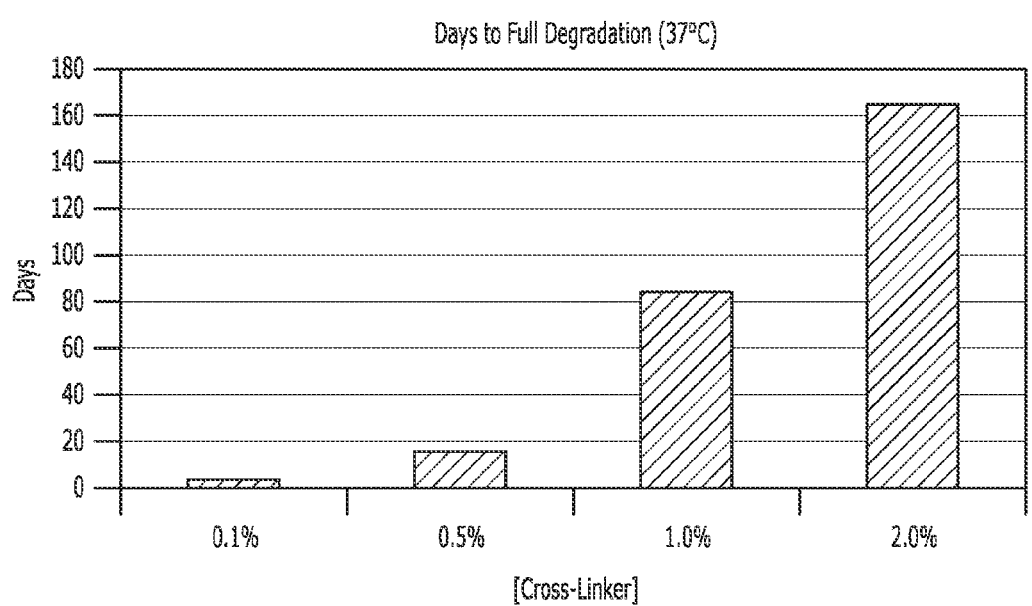
FIG. 3 is a graph showing time to full degradation for different polymer films.

Depending on film characteristics such as the amount of crosslinker used, degradation can take over 160 days in some cases, and less than 5 days in others. FIG. 3 illustrates the number of days required for the glycidyl-based cross-linker film samples to degrade.

Example 14

Tetra Ester Crosslinker

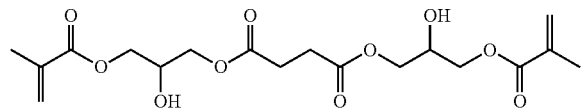 [SMILES: C=C(C)C(=O)OCC(O)COC(=O)CCC(=O)OCC(O)COC(=O)C(=C)C]

To a 200 mL pear-shaped flask, 10 g (84.8 mmol) of succinic acid, 40 g (0.689 mol) of allyl alcohol and 30 μL of 98% $H_2SO_4$ were added. The reaction mixture was refluxed for 6 hrs and then quenched by an addition of 25 mL of 1 M sodium carbonate solution. The product, diallyl succinate, was extracted with ethyl acetate, 4×50 mL. The organic phase was collected and dried with $MgSO_4$ and the solvent was then removed in vacuo to give 9.26 g of diallyl succinate.

To a 1 L round bottom flask, 5.2 g (26.3 mmol) of diallyl succinate and 20 g (0.116 mol) of meta-chloroperoxybenzoic acid (mCPBA) were dissolved in 400 mL of dichloromethane. The reaction mixture was refluxed at 40° C. overnight. The reaction mixture was then passed through an Amberlyst free base column to remove the by-product, m-chlorobenzoic acid. The solvent was removed under vacuum to give the crude. Chromatography using ethyl acetate in hexane from 5% to 20% at 210 nm gave the pure diglycidyl succinate.

To a 20 mL vial, 1.15 g (5 mmol) of diglycidyl succinate, 950 mg (11 mmol) of methacrylic acid and 1.5 g (7 mmol) of 1-butyl-3-methylimidazolium bromide ([bmim]Br) were added. The reaction mixture was stirred at 75° C. After 1 hr, the TLC showed no presence of the epoxide. The reaction mixture was suspended in 50 mL of 1 M sodium carbonate solution and the product was extracted with ethyl acetate, 3×50 mL. The organic layer was collected and dried over $MgSO_4$, and then concentrated under vacuum. The TLC ran with 50:50 ethyl acetate:dichloromethane showed only one spot. Two grams of tetra ester crosslinker was collected with 99% yield.

Example 15

Tetra Thioester Crosslinker

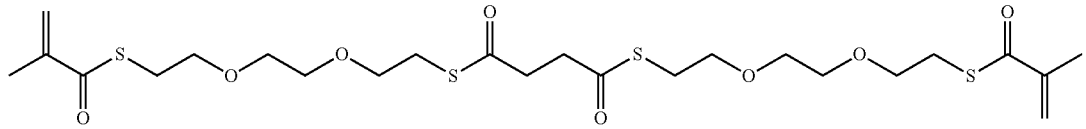 [SMILES: C=C(C)C(=O)SCCOCCOCCSC(=O)CCC(=O)SCCOCCOCCSC(=O)C(=C)C]

To a 500 mL 3-neck round bottom flask under Argon chilled at 0° C., 100 mL of dry THF was added. Under stirring, 20 g (0.11 mmol) of 2,2'-(ethylenedioxy)diehanthiol and 16 mL (0.09 mol) of diisopropylethylamine were added. To 40 mL of dry THF, 5 mL (0.045 mol) of succinyl chloride was dissolved. Under Argon, the solution was added drop wise into the reaction mixture at 0° C. via an addition funnel with vigorous stirring. Following the addition, the reaction mixture was stirred for 1 hour at 0° C. and then allowed to warm up to room temperature to stir overnight. The reaction mixture was then concentrated under vacuum. Flash chromatography with ethyl acetate in DCM from 0% to 15% at 254 nm gave the dithiol ester intermediate.

To a 250 mL 3-neck round bottom flask under Argon chilled at 0° C., 50 mL of dry THF was added. Under stirring, 3.17 g (7.1 mmole) of dithiol ester intermediate and 3.6 mL (20 mmole) of diisopropylethylamine were added. To 50 mL of dry THF, 2 mL (20 mmole) of methacryloyl chloride was dissolved. Under Argon, the solution was added drop wise into the reaction mixture at 0° C. via an addition funnel with vigorous stirring. Following the addition, the reaction mixture was stirred for 1 hr at 0° C. and then allowed to warm up to room temperature to stir overnight. The reaction mixture was then concentrated under vacuum. Flash chromatography with ethyl acetate in dichloromethane from 0% to 10% at 254 nm eluted the desired tetra thiol ester crosslinker from 4 min to 12 min. The mass spectrometry analysis gave 605.1 corresponding to $[M+Na]^+$ of the calculated mass of $C_{24}H_{38}O_8S_4$.

The preceding disclosures are illustrative embodiments. It should be appreciated by those of skill in the art that the devices, techniques and methods disclosed herein elucidate representative embodiments that function well in the practice of the present disclosure. However, those of skill in the art should, in light of the present disclosure, appreciate that many changes can be made in the specific embodiments that are disclosed and still obtain a like or similar result without departing from the spirit and scope of the invention.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

The use of the term "or" in the claims is used to mean "and/or" unless explicitly indicated to refer to alternatives only or the alternatives are mutually exclusive, although the disclosure supports a definition that refers to only alternatives and "and/or."

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects those of ordinary skill in the art to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above cited references and printed publications are herein individually incorporated by reference in their entirety.

Further, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A polymer film comprising:
   at least one monomer including at least one functional group; and
   at least one crosslinker selected from bis-glycidyl amino alcohol, bi-functionalized methacryloyl-Ala-Pro-Gly-Leu-AEE-methacrylate,

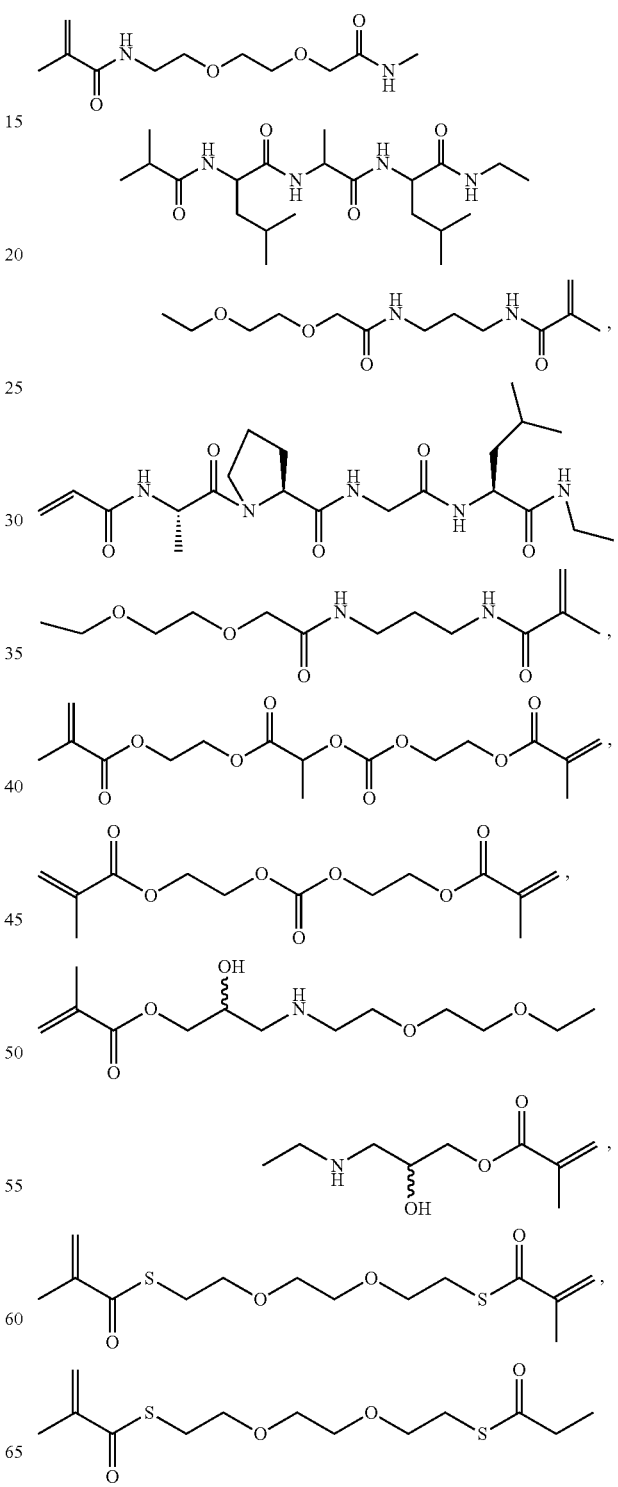

-continued

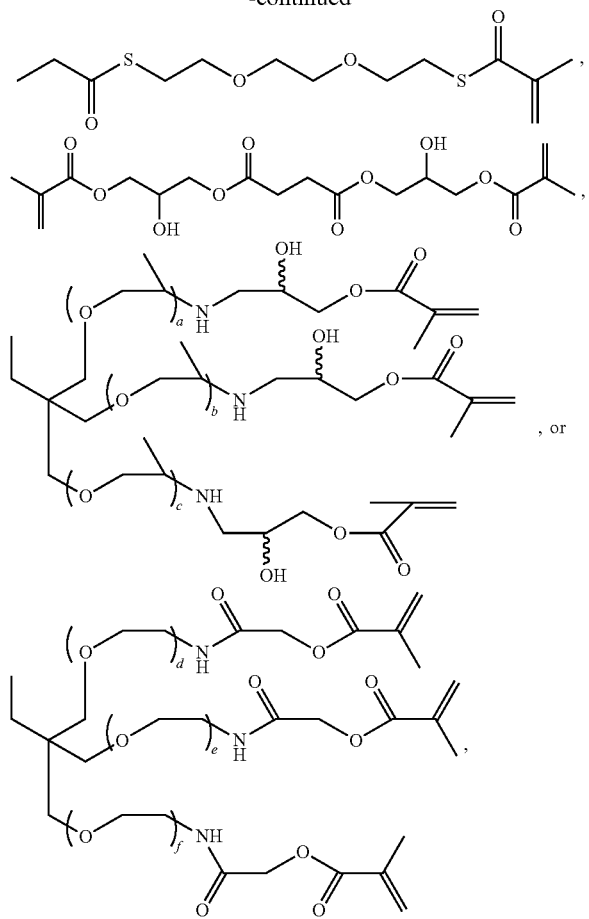

wherein a, b, c, d, e, and f are each independently 1-20;
wherein the polymer film has a thickness between about 40 μm and about 1,200 μm and is biodegradable.

2. The polymer film of claim 1, wherein the polymer film has a shape selected from a circle, square, rectangle, triangle, ellipse, or pentagon.

3. The polymer film of claim 1, wherein the at least one functional group is acrylate, acrylamide, methacrylate, or methacrylamide.

4. The polymer film of claim 1, wherein the at least one monomer includes an ionizable functional group.

5. The polymer film of claim 4, wherein the ionizable functional group is basic.

6. The polymer film of claim 4, wherein the ionizable functional group is acidic.

7. The polymer film of claim 1, wherein the at least one crosslinker includes at least two functional groups.

8. The polymer film of claim 1, wherein the crosslinker includes at least one linkage susceptible to degradation through hydrolysis or enzymatic action.

9. The polymer film of claim 8, wherein the at least one linkage is an ester, a thioester, a carbonate, a carbamate, a peptide cleavable by matrix metalloproteinases, a peptide cleavable by matrix collagenase, a peptide cleavable by matrix elastase, a peptide cleavable by matrix cathepsin, or a combination thereof.

10. The polymer film of claim 9, including a second crosslinker including a second linkage selected from an ester, a thioester, a carbonate, a carbamate, a peptide cleavable by matrix metalloproteinases, a peptide cleavable by matrix collagenases, a peptide cleavable by matrix elastases, and a peptide cleavable by matrix cathepsins.

11. The polymer film of claim 1, wherein the polymer film is substantially degraded within about 6 months of implantation.

12. The polymer film of claim 1, wherein the polymer film is substantially degraded within about 1 month of implantation.

13. The polymer film of claim 1, wherein the at least one monomer is acrylamide and the at least one crosslinker is bis-glycidyl amino alcohol.

14. The polymer film of claim 1, wherein the at least one monomer is acrylamide and the at least one crosslinker is bi-functionalized methacryloyl-Ala-Pro-Gly-Leu-AEE-methacrylate.

15. A method of making a polymer film comprising:
reacting a prepolymer solution including at least one monomer including at least one functional group, at least one crosslinker susceptible to degradation, and an initiator; and
forming the polymer film, wherein the polymer film has a thickness between about 40 μm and about 1,200 μm,
wherein the at least one crosslinker is selected from bis-glycidyl amino alcohol, bi-functionalized methacryloyl-Ala-Pro-Gly-Leu-AEE-methacrylate,

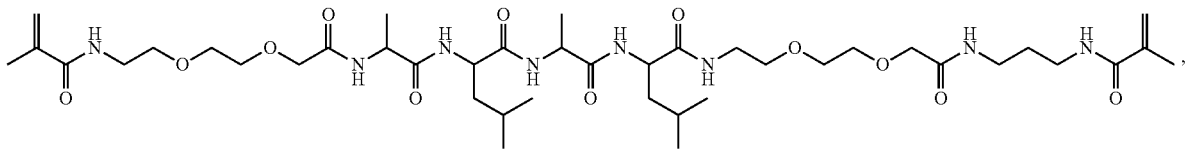

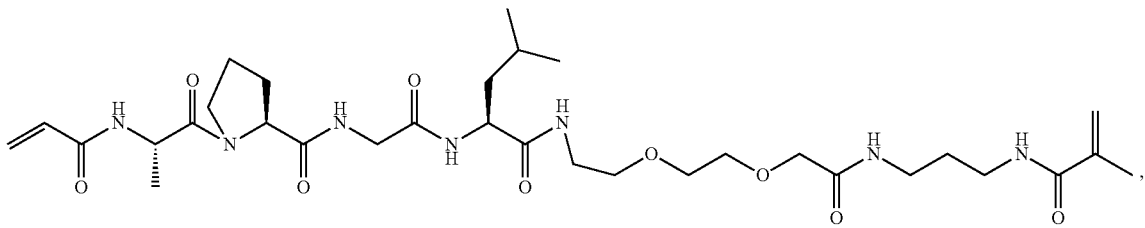

-continued

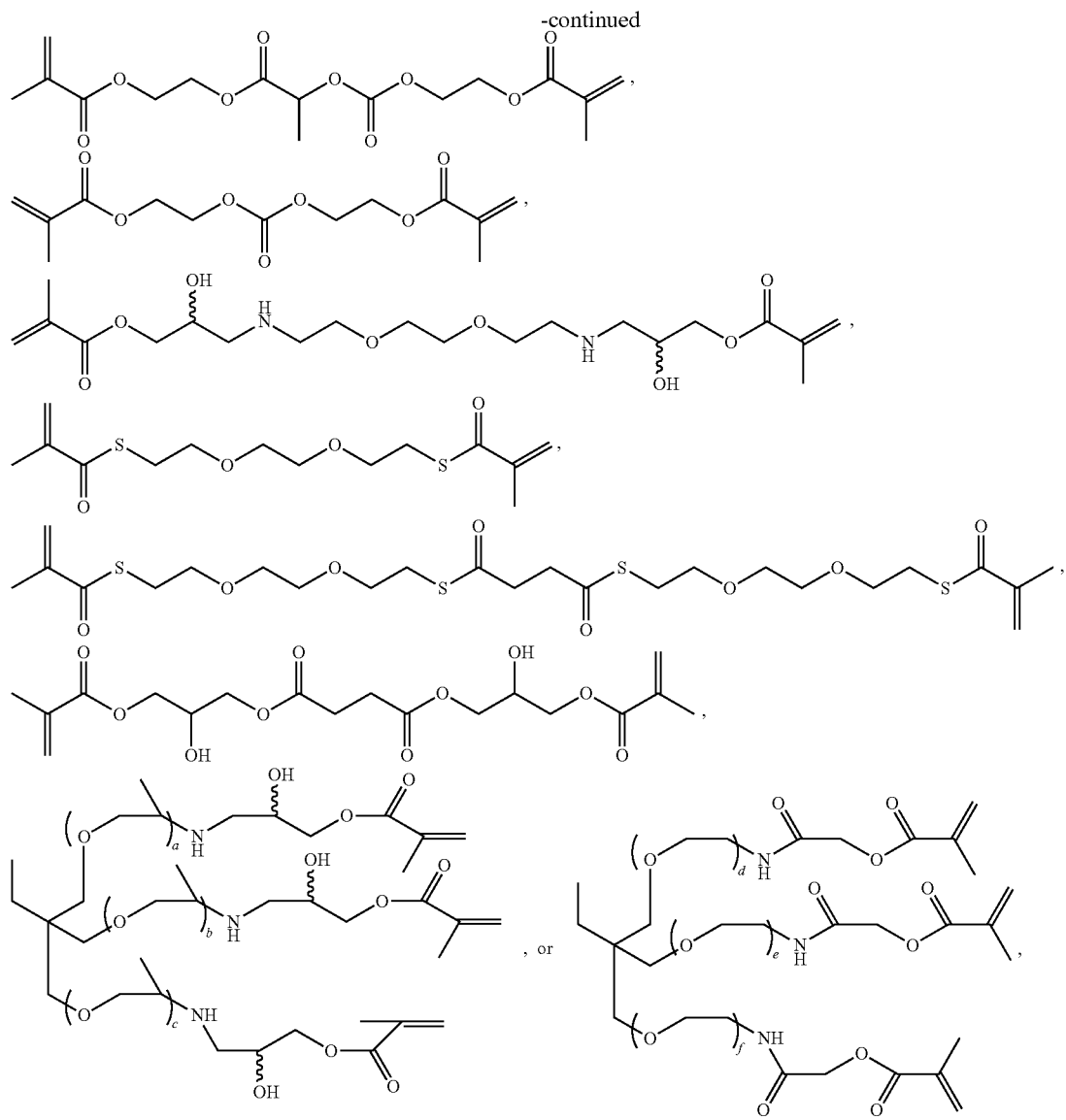

wherein a, b, c, d, e, and f are each independently 1-20.

16. The method of claim 15, wherein the film is formed between two plates including at least one spacer.

17. The method of claim 15, wherein the initiator is N,N,N',N'-tetramethylethylenediamine.

18. The method of claim 15, wherein the polymer film has a shape selected from a circle, square, rectangle, triangle, ellipse, or pentagon.

19. The method of claim 15, wherein the at least one functional group is acrylate, acrylamide, methacrylate, or methacrylamide.

20. The method of claim 15, wherein the polymer film is biodegradable.

21. The method of claim 20, wherein the polymer film is substantially degraded within about 1 month of implantation.

22. The method of claim 20, wherein the at least one monomer is acrylamide and the at least one crosslinker is bis-glycidyl amino alcohol.

23. The method of claim 20, wherein the at least one monomer is acrylamide and the at least one crosslinker is bi-functionalized methacryloyl-Ala-Pro-Gly-Leu-AEE-methacrylate.

* * * * *